United States Patent [19]

Peyman

[11] Patent Number: 5,185,152
[45] Date of Patent: Feb. 9, 1993

[54] METHOD AND APPARATUS FOR CONTROLLED RELEASE DRUG DELIVERY TO THE CORNEA AND ANTERIOR CHAMBER OF THE EYE

[76] Inventor: Gholam A. Peyman, 123 Walnut St., New Orleans, La. 70118

[21] Appl. No.: 747,432

[22] Filed: Aug. 13, 1991

Related U.S. Application Data

[63] Continuation of Ser. No. 462,485, Jan. 10, 1990, abandoned.

[51] Int. Cl.$^5$ .............................................. A61F 2/00
[52] U.S. Cl. .................................. 424/427; 424/428; 424/450; 424/469; 424/427; 424/429; 264/1.1; 264/2.6
[58] Field of Search ............... 424/427, 428, 450, 429, 424/469; 264/1.1, 2.6

[56] References Cited

U.S. PATENT DOCUMENTS

| | | | |
|---|---|---|---|
| 3,618,604 | 11/1971 | Ness | 128/260 |
| 3,960,150 | 6/1976 | Hussain et al. | 128/260 |
| 3,962,414 | 6/1976 | Michaels | 424/469 |
| 4,078,052 | 3/1978 | Papahadjopoulos | 424/36 |
| 4,241,046 | 12/1980 | Papahadjopoulos et al. | 424/19 |
| 4,264,155 | 4/1981 | Miyata | 351/160 H |
| 4,310,506 | 1/1982 | Baldeschwieler et al. | 424/1 |
| 4,350,676 | 9/1982 | Laties et al. | 424/7 |
| 4,365,050 | 12/1982 | Ivani | 527/312 |
| 4,388,428 | 6/1983 | Kuzma et al. | 523/106 |
| 4,447,562 | 5/1984 | Ivani | 523/105 |
| 4,452,925 | 6/1984 | Kuzma et al. | 523/106 |
| 4,515,736 | 5/1985 | Deamer | 264/4.3 |
| 4,522,803 | 6/1985 | Lenk et al. | 424/1.1 |
| 4,610,868 | 9/1986 | Fountain et al. | 424/1.1 |
| 4,663,233 | 5/1987 | Beavers | 428/412 |
| 4,713,446 | 12/1987 | DeVore et al. | 530/356 |
| 4,801,475 | 1/1989 | Halpern et al. | 427/338 |
| 4,863,457 | 9/1989 | Lee | 604/891.1 |
| 4,997,652 | 3/1991 | Wong | 424/428 |

OTHER PUBLICATIONS

O'Brien et al. (Journal of Cataract and Refractive Surgery 14:505–507, 1988).
Sawusch et al. (ARVO Abstracts; Invest Ophthalmol Vis Sci Suppl 29:228, 1988).
Unterman et al. (Journal of Cataract and Refractive Surgery 14:500–504, 1988).
Hobden et al. (Archives of Ophthalmology 106:1605–1607, 1988).
Poland et al. (Journal of Cataract and Refractive Surgery 14:489–491, 1988).
Sinclair (Proceedings of the Fifth International Symposium on Controlled Release of Bioactive Materials, Akron, Ohio, University of Akron Press, 1987).
Wada et al. (Journal of Bioactive and Compatible Polymers 3:126, 1988).
Langer et al. (Methods in Enzymology 12:399, 1985).

*Primary Examiner*—Thurman K. Page
*Assistant Examiner*—William E. Benston
*Attorney, Agent, or Firm*—Roylance, Abrams, Berdo & Goodman

[57] ABSTRACT

A method and device for delivering a drug to the cornea and anterior chamber of an eye are disclosed. A drug is entrapped in microspheres of poly(lactic acid), poly(glycolic acid), a copolymer of lactic acid and glycolic acid, poly(ethylene-vinyl acetate), or a mixture of poly(lactic acid) and poly(glycolic acid). The microspheres are combined with a hydrophilic polymer and placed in contact with the eye.

15 Claims, 2 Drawing Sheets

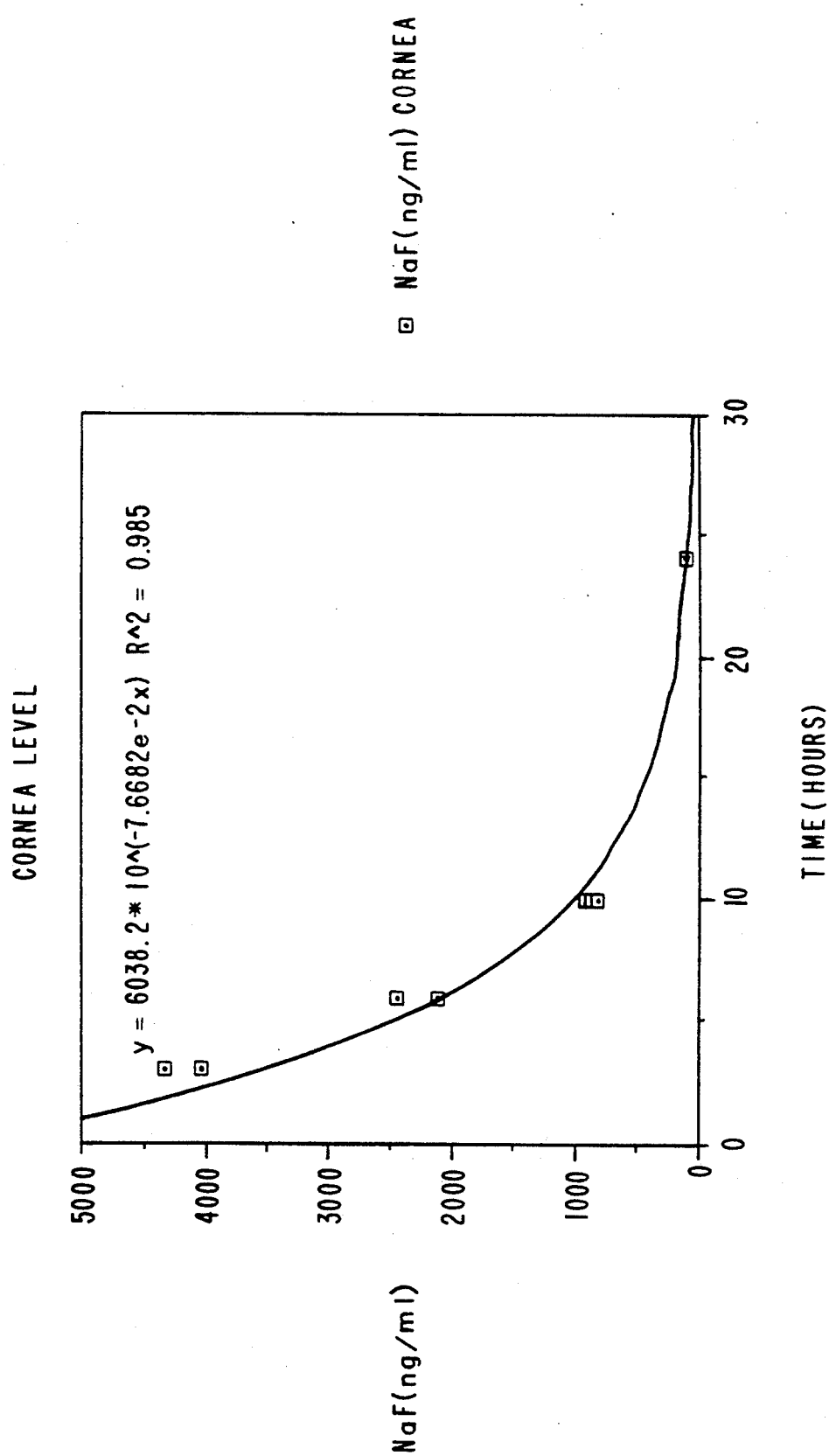

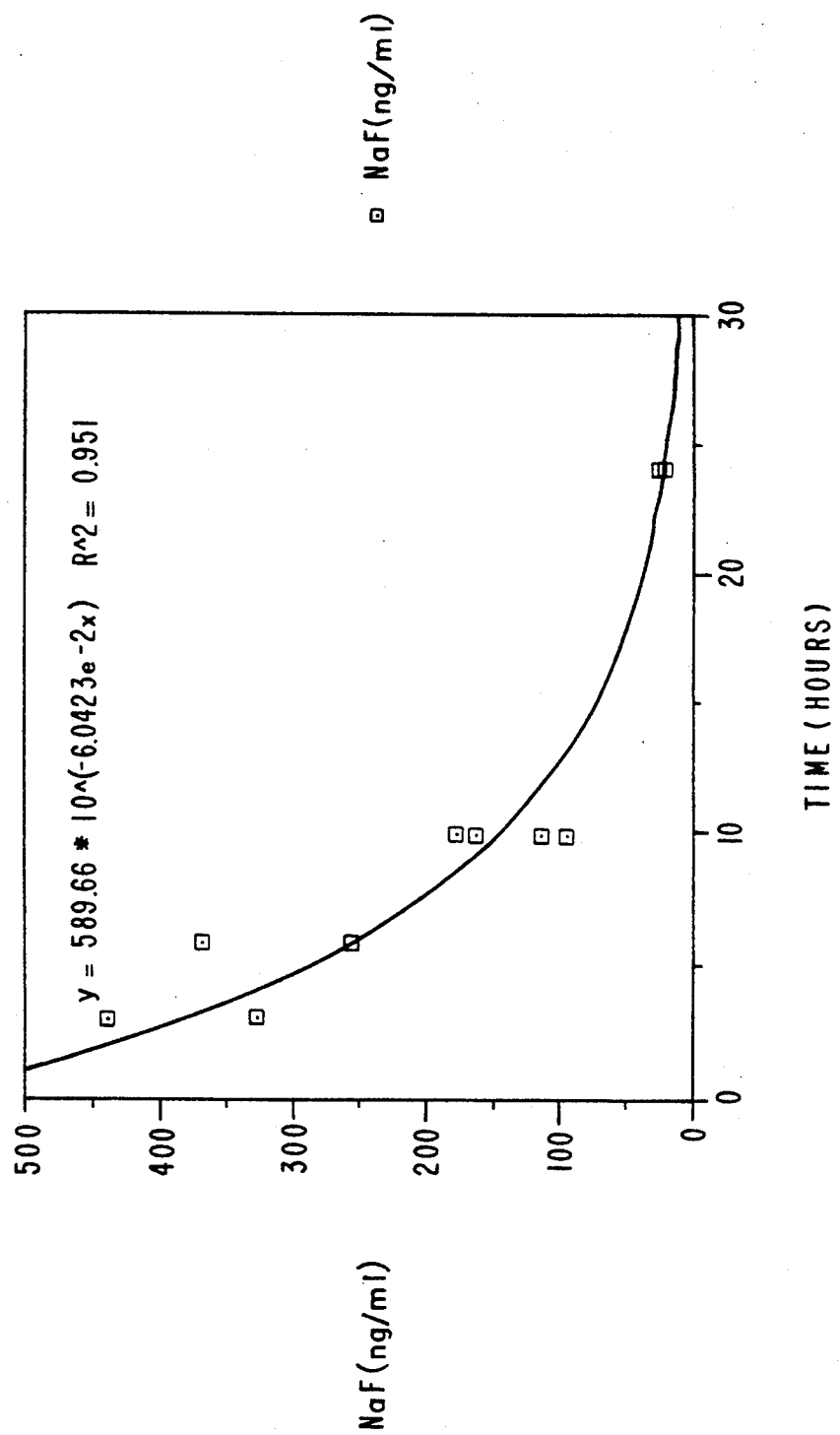

METHOD AND APPARATUS FOR CONTROLLED RELEASE DRUG DELIVERY TO THE CORNEA AND ANTERIOR CHAMBER OF THE EYE

This is a continuation of application Ser. No. 07/462,485 filed Jan. 10, 1990 now abandoned.

FIELD OF THE INVENTION

The invention relates to a method and apparatus for controlled release drug delivery to the cornea and anterior chamber of an eye. More particularly, the invention relates to a corneal shield combined with a drug for therapeutic treatment of the cornea and anterior chamber of the eye, wherein the drug is entrapped by microspheres.

BACKGROUND OF THE INVENTION

Previously, drugs for treatment of the cornea and anterior chamber of the eye have been applied by topical administration. This drug delivery technique is disadvantageous because it does not allow the drug to be dispensed in a continuous manner. The drug administered in the conjunctival sac is rapidly diluted by the tear fluid and repeated administration of the drug is required to make up for the loss.

Ophthalmic drugs may also be administered systemically. This method of administration also has the disadvantage that the drug reaches the desired concentration in the cornea and anterior chamber for only a short period of time, after which the drug is cleared from the circulation. Repeated application of a drug through systemic administration may produce undesired systemic toxicity.

In other medical areas, such as chemotherapy, the use of polymers for the slow release of drugs has been reported. The use of glycolide and lactide for slow release of chemotherapeutic agents has been reported previously by Sinclair (Proceedings of the Fifth International Symposium on Controlled Release of Bioactive Materials, Akron, Ohio, University of Akron Press, 1987); the use of bioactive oligomer microspheres containing anticancer agents has been reported in the Journal of Bioactive and Compatible Polymers (3:126, 1988); and the use of ethylene-vinyl acetate has been reported in Langer et al. Methods in Enzymology 12:399, 1985.

U.S. Pat. No. 3,960,150 to Hussain et al. discloses devices for the controlled continuous administration of a predetermined dosage of a drug to the eye including a device where the drug is confined in microcapsule reservoirs dispersed through a bioerodible matrix. The device is adapted for insertion in the sac of the eye bounded by the surfaces of the bulbar conjunctiva of the sclera of the eyeball and the palpebral conjunctiva of the lid. Such a device has the disadvantage with respect to drug delivery to the cornea that it does not allow a direct delivery of a drug to the cornea of the eye. Instead, the drug reaches the cornea only after dilution in the tear film.

Recently, it was found that hydrophilic plastic or collagen made in the form of a contact lens and placed on the cornea can enhance healing after corneal transplantation or other forms of corneal surgery such as refractive surgery. Collagen corneal shields have been developed as bandages to protect and promote the healing of the cornea. Collagen corneal shields are commonly stored in a dehydrated condition and are rehydrated before they are placed on the eye. When placed on the eye, the shields absorb ocular fluids and conform to the shape of the cornea. They then slowly dissolve, thereby lubricating the eye and promoting healing of the cornea.

It has also been found that hydrophilic contact lenses or corneal shields prolong the contact between drugs and the cornea and allow greater penetration of drugs into the anterior chamber of the eye. A lens or shield may serve as a drug delivery vehicle for topical administration of drugs by absorbing and slowly releasing topically applied drugs. Further, a collagen corneal shield may be soaked in a solution of a drug during rehydration so that the shield absorbs the drug. When the shield is applied to the cornea, the drug gradually permeates through the collagen shield toward the cornea and is released slowly and continuously as the collagen shield dissolves.

Recently, drug delivery systems using contact lenses made of hydrophilic plastic and collagen cornea shields have been tested in animals and humans as a means of providing a slow-release delivery of drugs to the cornea and anterior chamber. O'Brien et al. (Journal of Cataract and Refractive Surgery 14:505–507) reported a comparison of therapeutic soft contact lenses and collagen shields for administration of tobramycin to the cornea. Their results showed an enhanced penetration of tobramycin when delivered by corneal collagen shields. Similarly, Sawusch et al. (ARVO Abstracts; Invest Ophthalmol Vis Sci Suppl 29:228, 1988) reported successful treatment of bacterial keratitis with the use of collagen shields. In another study, Unterman et al. (Journal of Cataract and Refractive Surgery 14:500-504, 1988) reported therapeutic concentrations of tobramycin in the cornea and aqueous humor of rabbits up to eight hours after application of collagen shields containing the antibiotic. Further studies by Hobden et al. (Archives of Ophthalmology 106:1605–1607, 1988) showed the efficacy of tobramycin-soaked collagen shields in the treatment of Pseudomonas keratitis in rabbits; similar results were seen after 4 hours of treatment, compared to topical application of the drug every 30 minutes. Replacement of the dissolving antibiotic-soaked collagen shield with a new one provided further therapeutic effects similar to the effects achieved with repeated topical application of the drug. A study by Poland et al. (Journal of Cataract and Refractive Surgery 14:489–491, 1988) showed that collagen shields rehydrated in 4% tobramycin were well-tolerated clinically in the eyes of patients after corneal surgery and patients with nonsurgical epithelial healing problems.

The disadvantage of the use of the collagen shield alone as a drug delivery system is that the concentration of the drug that can be absorbed directly by the collagen shield is limited. Because of this, in order to achieve a sustained drug concentration over a long period of time, either the drug must be applied topically over a collagen shield that is in place on the eye, or collagen shields must be replaced regularly with new collagen shields hydrated in the drug. Both methods are therefore inconvenient, require monitoring of the patient, and involve a risk of patient noncompliance. Further, the use of the collagen shield as a direct drug delivery system is limited to water-soluble drugs, because lipid-soluble substances generally do not permeate the collagen shield.

Accordingly, there exists the need for a method and apparatus for slow release drug delivery of a high concentration of a drug directly to the cornea and anterior chamber of an eye over a long period of time. Further, there exists a need for a drug delivery system that allows either water-soluble or lipid-soluble drugs to be delivered to the cornea and anterior chamber. Further, it is desirable to have a drug delivery system that comprises substances that are not toxic to the eye.

SUMMARY OF THE INVENTION

Accordingly, a primary object of the present invention is to provide for the delivery of a uniform concentration of a drug directly to the cornea and anterior chamber of an eye over a long period of time.

A further object of the invention is to allow either water-soluble or lipid-soluble drugs to be delivered to the cornea.

Yet a further object of the invention of to provide a slow release drug delivery system that is not toxic to the eye.

The foregoing objects are basically attained by a method for delivering a drug to a cornea and anterior chamber of an eye comprising the steps of entrapping a drug in a drug release rate controlling material, thereafter combining the drug release rate controlling material with a hydrophilic polymer, and thereafter placing the hydrophilic polymer in contact with a cornea of an eye.

The foregoing objects are further attained by providing a method for delivering a drug to a cornea and anterior chamber of an eye comprising the steps of entrapping a drug in microspheres made of a polymer selected from the group consisting of poly(lactic acid), poly(glycolic acid), a copolymer of lactic acid and glycolic acid, and poly(ethylene-vinyl acetate), or a mixture of poly(lactic acid) and poly(glycolic acid), thereafter combining the microspheres with a hydrophilic polymer, and thereafter placing the hydrophilic polymer in contact with a cornea of an eye.

A device for delivering a drug to a cornea and anterior chamber of an eye is provided, the combination comprising a corneal shield made of a hydrophilic polymer, microspheres combined with the hydrophilic polymer, the microspheres being made of a polymer selected from the group consisting of poly(lactic acid), poly(glycolic acid), a copolymer lactic acid and glycolic acid and poly(ethylene-vinyl acetate), or a mixture of poly(lactic acid) and poly(glycolic acid), and a drug entrapped by the microspheres.

Other objects, advantages and salient features of the invention will become apparent from the following detailed description, which discloses the preferred embodiment of the invention.

BRIEF DESCRIPTION OF THE DRAWINGS

FIG. 1 is a graph showing the concentration of NaF on a cornea over time, the NaF being administered according to the method of this invention.

FIG. 2 is a graph showing the concentration of NaF in the anterior chamber of an eye over time, the NaF being administered according to the method of this invention.

DETAILED DESCRIPTION OF THE PREFERRED EMBODIMENT

The term "drug" as used herein refers to any water-soluble or lipid-soluble drug suitable for therapeutic use in the treatment of the cornea or anterior chamber of the eye. Examples include antibiotics, antifungal and antiviral agents, and immunosuppressants, such as cyclosporin. Examples of suitable drugs for therapy of the eye may be found in U.S. Pat. No. 3,960,150 to Hussain et al, the disclosure of which is incorporated herein by reference.

The drug release rate controlling material is preferably in the form of microspheres. The term "microspheres" as used herein refers to drug-entrapping particles, preferably in the size range of 0.25 to 10 microns, which are preferably made of a polymer selected from the group consisting of poly(lactic acid), poly(glycolic acid), a copolymer of lactic acid and glycolic acid, ethylene-vinyl acetate, or a mixture of poly(lactic acid) and poly(glycolic acid). Those skilled in the art can readily determine the appropriate monomer composition and molecular weight of the polymers for the desired rate of drug release. In the practice of this invention, any standard technique known in the art can be used to entrap the drug in the microspheres.

The drug release rate controlling material may also be in the form of lipid vesicles, known as liposomes. Examples of liposomes are disclosed in, for example, U.S. Pat. Nos. 4,078,052 to Papahadjopoulos; 4,241,046 to Papahadjopoulos et al; 4,310,506 to Baldeschwieler et al; 4,350,676 to Laties et al; 4,515,736 to Deamer; 4,522,803 to Lenk et al; and 4,610,868 to Fountain et al, the disclosures of which are hereby incorporated by reference.

The hydrophilic polymer of this invention is an organic or inorganic polymer, preferably collagen. Examples of other suitable hydrophilic polymers include polysaccharides, mucopolysaccharides, glycoproteins, hydrogel, and silicone, or combinations of these materials. Examples of suitable material may be found in U.S. Pat. Nos. 4,264,155, 4,713,446, 4,264,155, 4,388,428, 4,365,050, 4,663,233, 4,452,925, 4,447,562, 4,801,475, the disclosures of which are hereby incorporated by reference. Preferably, the hydrophilic polymer is transparent or semitransparent and nonirritating to the cornea. The hydrophilic polymer is molded or cut by methods known in the art to form a contact lens, bandage, or corneal shield suitable for placing in contact with the cornea of an eye. Collagen corneal shields have been approved by the FDA for use as corneal bandages and are commercially available. Corneal shields are generally shaped to conform to the shape of the cornea.

The microspheres may be combined with the hydrophilic polymer by one of two methods. In the first method, the microspheres are mixed with a salt solution and the hydrophilic polymer is soaked in this solution to absorb the microspheres. The hydrophilic polymer is then placed in contact with the eye. This method is especially useful for collagen corneal shields that are stored in a dehydrated condition and are rehydrated before use in the eye. By the second method, the microspheres are mixed directly with the hydrophilic polymer in the process of forming the corneal shield. The two methods may also be combined, that is, a corneal shield may be formed from a mixture of microspheres and hydrophilic polymer and the resulting cornea shield can then be soaked in a solution containing microspheres.

When placed in contact with the cornea of an eye, the polymeric material that makes up the microspheres slowly dissolves into monomers so that the drug entrapped by the microspheres is released, thereby providing a very uniform slow drug delivery to the cornea and the anterior chamber.

The following examples illustrate the practice of the invention and the preparation of the drug delivery device described above.

EXAMPLE 1

A mixture of poly(lactic acid) and poly(glycolic acid) and a drug are dissolved in a mixture of chloroform and acetone. The solutions are then emulsified in an aqueous solution of polyvinyl alcohol and stirred for 24 hours to evaporate the organic solvent. The solution is cleared with ultracentrifuge and lyophilized to a powder containing microspheres that include the entrapped drug. The powder is then mixed with a balanced salt solution to the desired concentration. The collagen shield is soaked in this solution for 10–15 minutes, and then the shield is applied to the cornea.

EXAMPLE 2

A lyophilized powder containing microspheres is prepared as described above. The lyophilized powder is then mixed with a collagen gel and the gel is formed into a collagen corneal shield wherein the microspheres including the entrapped drug are incorporated directly into the shield. The corneal shield is then applied to the cornea.

EXAMPLE 3

A collagen corneal shield was prepared as described in Example 1 by soaking a shield in a solution containing 3 mg/1 mL of NaF, the NaF being entrapped by microspheres made of 85% poly(lactic acid) and 15% poly(glycolic acid). The corneal shield was placed on the cornea of a rabbit and the concentration of NaF on the cornea and anterior chamber was measured over time. FIG. 1 shows the concentration of NaF as measured on the cornea; FIG. 2 shows the concentration of NaF as measured in the anterior chamber. The results, as set forth in FIG. 1 and FIG. 2, show a slow decay in the amount of NaF present on the cornea and anterior chamber, with significant measurable amounts still detectable after 24 hours.

Although the invention has been described in considerable detail with specific reference to certain advantageous embodiments thereof, variations and modifications can be made without departing from the scope of the invention as described in the specification and defined in the appended claims.

What is claimed is:

1. A method for delivering a drug directly to a cornea and anterior chamber of an eye comprising the steps of:
    entrapping a drug in microspheres made of a bioerodible polymer selected from the group consisting of poly(lactic acid), poly(glycolic acid), a copolymer of lactic acid an glycolic acid, and poly)ethylene-vinyl acetate), or a mixture of poly(lactic acid) and poly(glycolic acid),
    thereafter combining the microspheres with a hydrophilic polymer and forming a corneal shield for placement directly over the cornea, and
    thereafter placing the hydrophilic polymer corneal shield in contact with a cornea of an eye, whereby, as the microspheres dissolve, the drug is delivered directly to the cornea and anterior chamber of the eye.

2. The method of claim 1 wherein the hydrophilic polymer is collagen.

3. The method of claim 1 wherein the step of molding the hydrophilic polymer to a corneal shield occurs before the step of combining the microspheres with the hydrophilic polymer.

4. The method of claim 3 wherein the step of combining the microspheres with the hydrophilic polymer includes soaking the corneal shield in a solution containing the microspheres.

5. The method of claim 1 wherein the step of molding the hydrophilic polymer occurs after the step of combining the microspheres with the hydrophilic polymer.

6. The method of claim 1 wherein said hydrophilic polymer is transparent.

7. The method of claim 1 wherein said hydrophilic polymer is semi-transparent.

8. A device for delivering a drug directly to a cornea and anterior chamber of an eye, the combination comprising:
    a corneal shield made of a hydrophilic polymer to be placed in contact with a cornea of an eye,
    microspheres dispersed in said hydrophilic polymer, said microspheres being made of a bioerodible polymer selected from the group consisting of poly(lactic acid), poly(glycolic acid), a copolymer of lactic acid and glycolic acid, and poly)ethylene-vinyl acetate), or a mixture of poly(lactic acid) and poly(glycolic acid), and
    a drug entrapped by said microspheres.

9. The method of claim 8 wherein said hydrophilic polymer is collagen.

10. The method of claim 1 wherein the hydrophilic polymer is selected from the group consisting of collagen, polysaccharides, mucopolysaccharides, glycoproteins, hydrogel, and silicone, or a combination of these materials.

11. The method of claim 8 wherein the hydrophilic polymer is selected from the group consisting of collagen, polysaccharides, mucopolysaccharides, glycoproteins, hydrogel, and silicone, or a combination of these materials.

12. A method for delivering a drug directly to a cornea and anterior chamber of an eye comprising the steps of
    forming a solution of microspheres entrapping at least one drug, said microspheres being made of a polymer selected from the group consisting of polylactic acid, polyglycolic acid, copolymers of lactic acid and glycolic acid, polyethylene-vinyl acetate and mixtures of polylactic acid and polyglycolic acid,
    forming a corneal shield from a hydrophilic polymer for placement directly over the cornea,
    immersing the corneal shied in the solution of microspheres for sufficient time to absorb the microspheres, and
    placing the hydrophilic polymer corneal shield in contact with the cornea of an eye to dissolve the microspheres and release the drug directly to the cornea and anterior chamber of the eye.

13. The method according to claim 12, wherein the second forming step comprises forming the corneal shield in a dehydrated condition.

14. The method according to claim 12, wherein the second forming step comprises forming the corneal shield from collagen.

15. The method according to claim 12 and further comprising the steps of
    removing the corneal shield from the eye and immersing the corneal shield in a second solution of the microspheres for sufficient time for the corneal shield to absorb the microspheres; and
    placing the corneal shield in contact with the cornea to dissolve the microspheres and relates the drug directly to the cornea.

* * * * *

UNITED STATES PATENT AND TRADEMARK OFFICE
CERTIFICATE OF CORRECTION

PATENT NO. : 5,185,152
DATED : February 9, 1993
INVENTOR(S) : Gholam A. Peyman

It is certified that error appears in the above-identified patent and that said Letters Patent is hereby corrected as shown below:

Claim 15, line 8 (column 6, line 66), delete "relates" and insert -- release --.

Signed and Sealed this

Second Day of November, 1993

*Attest:*

BRUCE LEHMAN

*Attesting Officer*      *Commissioner of Patents and Trademarks*